(12) United States Patent
Ringler et al.

(10) Patent No.: US 6,551,593 B1
(45) Date of Patent: *Apr. 22, 2003

(54) TREATMENT OF INFLAMMATORY BOWEL DISEASE BY INHIBITING BINDING AND/OR SIGNALLING THROUGH α 4 β 7 AND ITS LIGANDS AND MADCAM

(75) Inventors: Douglas J. Ringler, Revere, MA (US); Dominic Picarella, Boston, MA (US); Walter Newman, Boston, MA (US)

(73) Assignee: Millennium Pharmaceuticals, Inc., Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/386,857

(22) Filed: Feb. 10, 1995

(51) Int. Cl.$^7$ .................. A61K 39/395; C07K 16/28

(52) U.S. Cl. ................. 424/143.1; 424/135.1; 424/133.1; 424/144.1; 424/154.1; 424/153.1; 424/173.1; 424/801; 424/810; 530/387.3; 530/388.22; 530/388.7; 530/388.75; 530/389.6; 530/867; 530/866; 530/868; 530/387.1

(58) Field of Search ................. 424/133.1, 135.1, 424/143.1, 144.1, 154.1, 153.1, 173.1, 801, 810; 530/387.3, 388.22, 388.7, 388.75, 389.6, 867, 866, 868, 387.1

(56) References Cited

U.S. PATENT DOCUMENTS

| | | | |
|---|---|---|---|
| 4,816,567 A | 3/1989 | Cabilly et al. | 530/387 |
| 5,225,539 A | 7/1993 | Winter | 530/387.3 |
| 5,403,919 A | 4/1995 | Butcher | 530/388.22 |
| 5,530,101 A | 6/1996 | Queen et al. | 530/387.3 |
| 5,538,724 A | 7/1996 | Butcher et al. | 424/152.1 |
| 5,558,864 A | 9/1996 | Bendig et al. | 424/133.1 |
| 5,585,089 A | 12/1996 | Queen et al. | 424/133.1 |
| 5,594,120 A | 1/1997 | Brenner et al. | 536/23.5 |
| 5,599,676 A | 2/1997 | Vonderheide et al. | 435/7.2 |
| 5,610,281 A | 3/1997 | Brenner et al. | 530/388.85 |
| 5,730,978 A | 3/1998 | Wayner | 424/144.1 |
| 5,840,299 A | 11/1998 | Bendig et al. | 424/133.1 |
| 5,932,214 A | 8/1999 | Lobb et al. | 424/144.1 |

FOREIGN PATENT DOCUMENTS

| | | |
|---|---|---|
| EP | 0 303 463 B1 | 11/1994 |
| JP | 6303990 | 11/1994 |
| WO | 90/07321 | 7/1990 |
| WO | 91/09967 | 7/1991 |
| WO | 93/02191 | 2/1993 |
| WO | 93/15764 | 8/1993 |
| WO | 93/23526 | 11/1993 |
| WO | 94/13312 | 6/1994 |
| WO | 94/16094 | 7/1994 |
| WO | 94/17828 | 8/1994 |
| WO | 95/19790 | 7/1995 |
| WO | 97/18838 | 5/1997 |

OTHER PUBLICATIONS

Sela, "Overview: antigens" from "Handbook of Exp. Immunol., Immunochemistry" ed. Weir et al., Balckwell Sci. Pub., 1986, pp. 1.1–1.7.*
Podolsky et al., J. Clin. Invest., 92:372–380, 1993.*
Berlin et al., Cell, 74: 185–195, 1993.*
Osband et al., Imm Today, 11: 103–105, 1990.*
Harris et al., TIBTECH, 11:42–44, 1993.*
Waldmann, Science, 252: 1657–1662, 1991.*
Tidswell, M., et al., "Structure–Function Analysis of the Integrin $β_7$ Subunit," *J. Immunol.*, 159:1497–1505 (1997).
Pulido, R., et al., "Functional Evidence for Three Distinct and Independently Inhibitable Adhesion Activities Mediated by the Human Integrin VLA–4," *J. Biol. Chem.*, 266(16):10241–10245 (1991).
Sánchez–Madrid, F., et al., "VLA–3: A Novel Polypeptide Association Within the VLA Molecular Complex: Cell Distribution and Biochemical Characterization," *Eur. J. Immunol.*, 16:1343–1349, (1986).
Ringler, D.J. et al., "Cellular Localization of Simian Immuno–deficiency Virus in Lymphoid Tissues I. Immunohistochemistry and Electron Microscopy," *American Journal of Pathology* 134(2):373–383 (1989).
Strober, Warren and Ehrhardt, Rolf O., "Chronic Intestinal Inflammation: An Unexpected Outcome in Cytokine or T Cell Receptor Mutant Mice," *Cell* 75:203–205 (1993).
Sadlack, Benjamin et al., "Ulcerative Colitis–like Disease in Mice with a Disrupted Interleukin–2 Gene," *Cell* 75:253–261 (1993).
Hamann, Alf et al., "Role of $α_4$–Integrins in Lymphocyte Homing to Mucosal Tissues In Vivo," *Journal of Immunology* 152:3282–3293 (1994).
Cooper, Harry S. et al., "Clinicopathologic Study of Dextran Sulfate Sodium Experimental Murine Colitis," *Laboratory Investigation* 69(2):238–249 (1993).
Okayasu, Isao et al., "Novel Method in the Induction of Reliable Experimental Acute and Chronic Ulcerative Colitis in Mice," *Gastroenterology* 98:694–702 (1990).
Podolsky, Daniel K., "Inflammatory Bowel Disease (First of Two Parts)," *The New England Journal of Medicine* 325 (13):928–937 (1991).
Podolsky, Daniel K., "Inflammatory Bowel Disease (Second of Two Parts)," *The New England Journal of Medicine* 325 (14):1008–1016 (1991).

(List continued on next page.)

Primary Examiner—Ronald B. Schwadron
(74) Attorney, Agent, or Firm—Hamilton, Brook, Smith & Reynolds, P.C.

(57) ABSTRACT

The invention relates to the treatment of individuals suffering from a disease associated with leukocyte recruitment to the gastrointestinal tract or other tissues as a result of binding of leukocytes to gut-associated endothelium expressing the molecule MAdCAM (such as inflammatory bowel disease), comprising administering to the individual an effective amount of an antibody which inhibits the binding of leukocytes to endothelial MAdCAM.

22 Claims, 6 Drawing Sheets

OTHER PUBLICATIONS

Springer, Timothy A., "The Sensation and Regulation of Interactions with the Extracellular Environment: The Cell Biology of Lymphoctye Adhesion Receptors," *Ammu. Rev. Cell Biol.* 6:359–402 (1990).

Dueñas, Marta and Borrebaeck, Carl A.K., "Clonal Selection and Amplification of Phage Displayed Antibodies by Linking Antigen Recognition and Phage Replication," *Bio/Technology* 12:999–1002 (1994).

Picker, Louis, J. and Butcher, Eugene C., "Physiological and Molecular Mechanisms of Lymphocyte Homing," *Annu. Rev. Immunol.* 10:561–591 (1992).

Hynes, Richard O., "Integrins: Versatility, Modulation, and Signaling in Cell Adhesion," *Cell* 69:11–25 (1992).

Michie, Sara A. et al., "The Human Peripheral Lymph Node Vascular Addressin, An Inducible Endothelial Antigen Involved in Lymphocyte Homing," *American Journal of Pathology* 143(6):1688–1698 (1993).

Schweighoffer, Tamas et al., "Selective Expression of Integrin α4β7 on a Subset of Human CD4+Memory T Cells with Hallmarks of Gut–Trophism," *The Journal of Immunology* 151(2):717–729 (1993).

Springer, Timothy A. "Traffic Signals for Lymphocyte Recirculation and Leukocyte Emigration: The Multistep Paradigm," *Cell* 76:301–314 (1994).

Briskin, Michael J. et al., "MadCAM–1 has homology to immunoglobulin and mucin–like adhesion receptors and to IgA1," *Nature* 363:461–463 (1993).

Salmi, Marko et al., "Aberrant Binding of Lamina Propria Lymphocytes to Vascular Endothelium in Inflammatory Bowel Diseases," *Gastroenterology* 106:596–605 (1994).

Silber, Alexandra et al., "Recruitment of Lymphocytes during Cutaneous Delayed Hypersensitivity in Nonhuman Primates is Dependent on E–Selectin and Vascular Cell Adhesion Molecule 1," *J. Clin. Invest.* 93:1554–1563 (1994).

Salmi, Marko et al., "Dual Binding Capacity of Mucosal Immunoblasts to Mucosal and Synovial Endothelium in Humans: Dissection of the Molecular Mechanisms," *J. Exp. Med.* 181:137–149 (1995).

Andrew, David P. et al., "Distinct but Overlapping Epitopes Are Involved in $\alpha_4\beta_7$–Mediated Adhesion to Vascular Cell Adhesion Molecule–1, Mucosal Addressin–1, Fibronectin, and Lymphocyte Aggregation," *Journal of Immunology* 153:3847–3861 (1994).

Lazarovits, Andrew I. et al., "I. A Monoclonal Antibody, Anti–Act I, Defines a New Late Lymphocyte Activation Antigen", *Journal of Immunology* 133(4): 1857–1862 (1984).

Schweighoffer, Tamas et al., "Selective Expression of Integrin α4β7 on a Subset of Human CD4+ Memory T Cells with Hallmarks of Gut–Trophism[1]", *Journal of Immunology* 151(2): 717–729 (1993).

Erle, David J. et al., "Expression and Function of the MAdCAM–1 Receptor, Integrin α4β7, on Human Leukocytes[1]", *Journal of Immunology* 153:517–528 (1994).

Berg, E.L., et al., "L–selectin–mediated lymphocyte rolling on MAdCAM–1", *Nature* 366:695–698 (1993).

Berlin, C., et al., "α4 Integrins Mediate Lymphocyte Attachment and Rolling under Physiologic Flow", *Cell* 80:413–422 (1995).

Bednarczyk, J.L., et al., "Identification of a Combinatorial Epitope Expressed by the Integrin α4β1 Heterodimer Involved in the Regulation of Cell Adhesion," *J. Biol. Chem.*, 269(11):8348–8354 (1994).

Briskin, M.J. et al., "Structural Requirements for Mucosal Vascular Addressin Binding to Its Lymphocyte Receptor α4β7", *J. Immunol.*, 156:719–726 (1996).

Yang, Y. et al., "Construction and Adhesive Properties of a Soluble MAdCAM–1–Fc Chimera Expressed in a Baculovirus System: Phylogenetic Conservation of Receptor–Ligand Interaction", *Scand. J. Immunol.*, 42:235–247 (1995).

Rudinger, J., *In Peptide Hormones*, Parsons, J.A., ed., (University Park Press, Baltimore, MD), pp. 1–7 (1976).

Lazarovits, A. I and Karsh, J., "$\alpha^4\beta_7$ Integrin in Rheumatoid Arthritis", *In Leucocyte Typing V—White Cell Differentiation Antigens*, S.F. Schlossman et al., eds,. (Oxford: Oxford University Press), pp. 1686, 1687 (1995).

Postigo, A.A., et al., "α4β7 Integrin Mediates B Cell Binding to Fibronectin and Vascular Cell Adhesion Molecule–1", *J. Immunol.*, 151(5):2471–2483 (1993).

Lazarovits, A. I. and Karsh, J., "Differential Expression in Rheumatoid Synovium and Synovial Fluid of α4β7 Integrin—A Novel Receptor for Fibronectin and Vascular Cell Adhesion Molecule–1", *J. Immunol.*, 151(11):6482–6489 (1993).

Riechmann, L., et al., "Reshaping Human Antibodies for Therapy", *Nature*, 332:323–327 (1988).

Bendig, M.M., "Humanization of Rodent Monoclonal Antibodies by CDR Grafting", *METHODS: A Companion to Methods in Enzymology*, 8:83–93 (1995).

Page, M.J. and Sydenham, M.A., "High Level Expression of the Humanized Monoclonal Antibody Campath–1H in Chinese Hamster Ovary Cells", *Bio/Technology*, 9:64–68 (1991).

Yacyshyn, B.R., et al., "Crohn's Disease, Ulcerative Colitis, and Normal Intestinal Lymphocytes Express Integrins in Dissimilar Patterns", *Gastroenterology*, 107:1364–1371 (1994).

Pals, S.T., et al., "Expression of the Mucosal Homing Receptor α4β7 in Malignant Lymphomatous Polyposis of the Intestine", *Gastroenterology*, 107:1519–1523 (1994).

Teague, T.K., et al., "Integrin α4β7 Co–Stimulation of Human Peripheral Blood T Cell Proliferation", *Cell Ad. Comm.*, 2:539–547 (1994).

Tiisala, S., et al., "$\alpha_E\beta_7$ and $\alpha_4\beta_7$ Integins Associated with Intraepithelial and Mucosal Homing, are Expressed on Macrophages", *Eur. J. Immunol.*, 25:411–417 (1995).

Wan, H.C., et al., "Expression of α4β7 Integrin on Eosinophils and Modulation of α4–Integrin–Mediated Eosinophil Adhesion via CD4", *Int. Arch. Allergy Immunol.*, 107:343–344 (1995).

Kettleborough, C.A., et al., "Humanization of a Mouse Monoclonal Antibody by CDR–grafting: The Importance of Framework Residues on Loop Conformation", *Protein Engng.*, 4(7):773–783 (1991).

Shaw, S.K., et al., "Molecular Cloning of the Human Mucosal Lymphocyte Integrin $\alpha^E$ Subunit", *J. Biol. Chem.*, 269(5):016–6025 (1994).

Parker, C.M., et al. "A family of β7 integrins on human mucosal lymphocytes", *Proc. Natl. Acad. Sci*, USA, 89:1924–1928 (1992).

Roberts, K. and Kilshaw, P. J., "The mucosal T cell integrin $\alpha_{M290}\beta 7$ recognizes a ligand on mucosal epithelial cell lines", *Eur. J. Immunol.* 23:1630–1635 (1993).

* cited by examiner

TREATMENT OF INFLAMMATORY BOWEL DISEASE BY INHIBITING BINDING AND/OR SIGNALLING THROUGH α 4 β 7 AND ITS LIGANDS AND MADCAM

BACKGROUND OF THE INVENTION

Inflammatory bowel disease (IBD), such as ulcerative colitis and Crohn's disease, for example, can be a debilitating and progressive disease involving inflammation of the gastrointestinal tract affecting an estimated two million people in the United States. Symptoms include abdominal pain, cramping, diarrhea and rectal bleeding. IBD treatments have included anti-inflammatory drugs (such as, corticosteroids and sulfasalazine), immunosuppressive drugs (such as, 6-mercaptopurine, cyclosporine and azathioprine) and surgery (such as, colectomy). Podolsky, *The New England Journal of Medicine*, 325:928–937 (1991) and Podolsky, *The New England Journal of Medicine*, 325:1008–1016 (1991).

Some studies have suggested that the cell adhesion molecule, ICAM-1, mediates leukocyte recruitment to inflammatory sites through adhesion to leukocyte surface ligands, i.e. Mac-1, LFA-1 or $\alpha 4\beta 2$ (Springer, *Nature*, 346:425–434 (1990)). In addition, vascular cell adhesion molecule-1 (VCAM-1), recognizing the $\alpha 4\beta 1$ integrin (VLA-4), has been reported to play a role in in vivo leukocyte recruitment as well (Silber et al., *J. Clin. Invest.* 93:1554–1563 (1994)). It has been proposed that IBD can be treated by blocking the interaction of ICAM-1 with LFA-1 or Mac-1 or VCAM-1 with $\alpha 4\beta 1$ (e.g., WO 93/15764). However, these therapeutic targets are likely involved in inflammatory processes in multiple organs, and a functional blockade would likely result in systemic immune dysfunction.

Mucosal addressin MAdCAM, a mucosal vascular adhesion molecule, is a 58-66K glycoprotein adhesion receptor for lymphocytes which is distinct from VCAM-1 and ICAM-1 (Briskin et al., *Nature*, 363:461–463 (1993)). In contrast to VCAM-1 and ICAM-1, MAdCAM is preferentially expressed in the gastrointestinal tract, binds the $\alpha 4\beta 7$ integrin (also called LPAM-1 and CD49d/CD⁻) found on lymphocytes, and participates in the homing of these cells to mucosal sites, such as Peyer's patches in the intestinal wall (Hamann et al., *Journal of Immunology*, 152:3282–3293 (1994)). The use of inhibitors to the binding of MAdCAM to the receptor, $\alpha 4\beta 7$, in the treatment of diseases such as IBD has not been suggested.

SUMMARY OF THE INVENTION

The invention relates to the treatment of individuals suffering from a disease associated with leukocyte recruitment to the gastrointestinal tract as a result of binding of leukocytes to gut-associated endothelium expressing the molecule MAdCAM, comprising administering to the individual an effective amount of a compound, such as an antibody, which inhibits the binding of leukocytes to endothelial MAdCAM. The antibody is preferably monoclonal, chimeric and/or humanized or an antigen binding fragment thereof, and inhibits adhesion of leukocytes expressing an integrin containing the β7 chain (such as α4β7) to endothelium expressing MAdCAM. In one embodiment, the monoclonal antibody or antigen binding fragment thereof has the antigenic specificity of a monoclonal antibody selected from the group consisting of FIB 21, FIB 30, FIB 504 and ACT-1. Inflammatory bowel diseases, such as but not limited to ulcerative colitis, Crohn's disease, Pouchitis, celiac disease, microscopic or collagenous colitis, and eosinophilic gastroenteritis can be treated according to the claimed method.

DETAILED DESCRIPTION OF THE INVENTION

Figure 1A:
FIGS. 1a and 1b are graphic illustrations of histologic scores of inflammatory activity and epithelial injury from left (descending) and right (ascending) colon of mice exposed to 10 days of DSS in their drinking water. Three groups of mice are shown, consisting of groups receiving an irrelevant rat IgG2a antibody, FIB21, or FIB30 antibodies.

The invention relates to the discovery that diseases associated with leukocyte recruitment to the gastrointestinal tract, such as IBD, or other mucosal tissues can be treated by inhibiting MAdCAM binding to the α4β7 integrin or triggering of α4β7-mediated cellular responses. Compounds which inhibit binding include antibodies or antigen binding fragments thereof which bind MAdCAM and/or the α4β7 integrin. Antibodies which can be used in the method include recombinant or non-recombinant polyclonal, monoclonal, chimeric, humanized and/or anti-idiotypic antibodies.

Monoclonal antibodies that bind MAdCAM or α4β7 have been described. For example, MECA 367 is an anti-MAdCAM antibody of the IgG2a subtype and is described in Gallatin et al., *Nature*, 304:30 (1983) and Michie et al., *Am. J. Pathol.* 143:1688–1698 (1993). ACT-1 is a monoclonal antibody which binds the α4β7 integrin (Lazarovits et al., *Journal of Immunology*, 133:1857 (1984) and Schweighoffer et al., *Journal of Immunology*, 151:717–729 (1993)). FIB 21 binds the β7 chain is described and characterized in Berlin et al., *Cell* 74:184–195 (1993); Andrew, D. P. et al., *J. Immunol.* 153:3847–3861 (1994)). Other monoclonal antibodies, such as antibodies which bind to the same or similar epitopes as the antibodies described above, can be made according to methods known in the art, such as Kohler et al., *Nature*, 256:495–497 (1975), Harlow et al., 1988, *Antibodies: A Laboratory Manual*, (Cold Spring Harbor, N.Y.) or *Current Protocols in Molecular Biology*, Vol. 2 (Supplemental 27, Summer '94), Ausubel et al., Eds. (John Wiley & Sons: New York, N.Y.), Chapter 11 (1991). For example, antibodies can be raised against an appropriate immunogen in a suitable mammal. Immunogens include, for example, MAdCAM α4β7 or immunogenic fragments thereof. The mammal can be a mouse, rat, rabbit or sheep, for example. The antibody-producing cell (e.g., a lymphocyte) can be isolated from, for example, the lymph nodes or spleen of the mammal. The cell can then be fused to a suitable immortalized cell (e.g., a myeloma cell line), thereby forming a hybridoma. The fused cells can be isolated employing selective culturing techniques. Cells which produce antibodies with the desired specificity can be selected by a suitable assay (e.g., ELISA).

In one embodiment, the immunogen can be an antibody which binds, for example, MAdCAM $\alpha 4\beta 7$ or immunogenic fragments thereof. The antibody raised thereby can be an anti-idiotypic antibody, which can also be used in the present invention.

Single chain antibodies, and chimeric, humanized or primatized (CDR-grafted or resurfaced, such as, according to EP 592406, Apr. 13, 1994) antibodies, as well as chimeric or CDR-grafted single chain antibodies, comprising portions derived from different species, can also be used in the invention. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., BioTechnology, 10:1455–1460 (1992), regarding primatized antibody, and Ladner et al., U.S. Pat. No. 4,946,778 and Bird, R. E. et al., *Science*, 242:423–426 (1988)) regarding single chain antibodies.

In addition, functional fragments of antibodies, including fragments of chimeric, humanized, primatized or single chain antibodies, can also be produced. Functional fragments of the foregoing antibodies retain at least one binding function of the full-length antibody from which they are derived and, preferably, retains the ability to inhibit interaction. For example, antibody fragments capable of binding to the $\alpha 4\beta 7$ integrin; MAdCAM or portion thereof include, but are not limited to, Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Alternatively, antibodies can be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the $CH_1$ domain and hinge region of the heavy chain.

Antibodies and antigen binding fragments thereof which can be used in the claimed method include antibodies which bind to MAdCAM and/or $\alpha 4\beta 7$, such as the $\beta 7$ chain. For example, antibodies from the group including FIB 21, FIB 30, FIB 504 and ACT-1 and mixtures thereof can be administered. Alternatively or in addition, antigen fragments of these antibodies can be administered.

Murine ACT-1 Hybridoma cell line, which produces the murine ACT-1 monoclonal antibody, was deposited under the provisions of the Budapest Treaty on Aug. 22, 2001, on behalf Millennium Pharmaceuticals, Inc., 75 Sidney Street, Cambridge, Mass. 02139, U.S.A., at the American Type Culture Collection, 10801 University Boulevard, Manassas, Va. 20110-2209, U.S.A., under Accession No. PTA-3663.

Compounds which inhibit the binding of MAdCAM and the $\alpha 4\beta 7$ integrin can be administered according to the claimed method in the treatment of diseases which are associated with leukocyte (such as lymphocyte or monocyte) recruitment to the gastrointestinal tract or other tissues as a result of binding of leukocytes to gut-associated endothelium expressing the molecule MAdCAM. Diseases which can be treated accordingly include inflammatory bowel disease, such as ulcerative colitis, Crohn's disease, Celiac disease (nontropical Sprue), enteropathy associated with seronegative arthropathies, microscopic or collagenous colitis, eosinophilic gastroenteritis, or pouchitis resulting after proctocolectomy and ileoanal anastomosis. In one embodiment, more than one monoclonal antibody which inhibits the binding of leukocytes to endothelial MAdCAM is administered. Alternatively, a monoclonal antibody which inhibits the binding of leukocytes to endothelial ligands is administered in addition to an anti-MAdCAM or anti-$\beta 7$ antibody. For example, an antibody that inhibits the binding of leukocytes to an endothelial ligand other than MAdCAM, such as an anti-ICAM-1 or anti-VCAM-1 antibody can also be administered. In another embodiment, an additional pharmacologically active ingredient (such as a steroid) can be administered in conjunction with the antibody of the present invention.

A variety of routes of administration are possible including, but not necessarily limited to parenteral (e.g., intravenous, intraarterial, intramuscular, subcutaneous injection), oral (e.g., dietary), topical, inhalation (e.g., intrabronchial, intranasal or oral inhalation, intranasal drops), or rectal, depending on the disease or condition to be treated. Parenteral administration is a preferred mode of administration.

Formulation of a compound to be administered will vary according to the route of administration selected (e.g., solution, emulsion, capsule). An appropriate composition comprising the compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, *Remington's Pharmaceutical Science*, 16th Edition, Mack, Ed. 1980). For inhalation, the compound is solubilized and loaded into a suitable dispenser for administration (e.g., an atomizer, nebulizer or pressurized aerosol dispenser).

The compound is administered in an amount which will inhibit binding of MAdCAM to the $\alpha 4\beta 7$ integrin. The compounds can be administered in a single dose or multiple doses. The dosage can be determined by methods known in the art and is dependent, for example, upon the individual's age, sensitivity, tolerance and overall well-being. Suitable dosages can be from 0.1–1.0 mg/kg body weight per treatment.

The subject invention will now be illustrated by the following examples, which are not intended to be limiting in any way.

EXEMPLIFICATION

Example 1

Inhibition of Lymphocyte Recruitment to Colon Induction of Colitis in Mice

BALB/c mice were given access to a 5% solution of dextran sodium sulfate (DSS) in their drinking water for a period of 10 days, as previously described (*Lab. Invest.* 69:238–249, 1993). During this time period, the mice developed clinical symptoms of colitis including softening of stools and bloody diarrhea. Multifocal epithelial injury and ulceration, similar to ulcerative colitis in humans, was evident on histologic examination of colonic mucosa from affected mice. Moreover, affected mice lost 20–30% of their initial body weight by day 10.

Antibody blockade of β7 and MAdCAM Interactions

To determine the efficacy of β7-specific antibodies in blocking the recruitment of lymphocytes to the colon, BALB/c mice were given daily intraperitoneal (i.p.) injections of 100 μg of monoclonal antibodies against β7, consisting of either FIB21 or FIB30 in saline, as previously characterized and described (Berlin, C., et al., *Cell* 74:185–195, 1993; Michie, S. A., et al., *Am. J. Pathol.* 143:1688–1698, 1993; Hamann, A., et al., *J. Immunol.* 152:3282–3293, 1994) or an isotype-matched control rat monoclonal antibody at the same dose (Andrew et al., supra) over the 10 day course of DSS treatment.

Methods of Evaluation

Two methods were used to evaluate efficacy of the antibody therapy to inhibit leukocyte infiltration and mucosal injury in the colitic mouse. In the first method, treatment was judged histologically by two blinded observers using a scoring system for the evaluation of epithelial injury and degree of leukocyte cellular infiltration (Table 1). For this assessment, colon tissue was first fixed in 10% neutral buffered formalin, dehydrated, embedded in paraffin, sectioned, and the sections were stained with hematoxylin and eosin prior to examination.

TABLE

PATHOLOGY EVALUATION

| Grade | Definition |
|---|---|
| INFLAMMATION | |
| Normal (0) | Absence of clusters of polymorphonoclear leukocytes (PMNs) or mononuclear cells in the lamina propria; absence of intraepithelial PMNs |
| Mild (1) | Focal aggregates of PMNs and/or mononuclear cells in the lamina propria (equivocal or slight) or presence of isolated intraepithelial PMNs in 3 or fewer crypts per cross-section |
| Moderate (2) | Focal aggregates of PMNs and/or mononuclear cells in the lamina propria (multi-focal or diffuse 2–5X) or intraepithelial PMNs in more than 3 crypts per cross-section |
| Severe (3) | Diffuse infiltration of PMNs or mononuclear cells in the lamina propria (diffuse >5X) or crypt abscesses |
| STRUCTURAL OR EPITHELIAL ALTERATIONS | |
| Normal (0) | Tight crypts, no erosion, columnar epithelial cells |
| Mild (1) | Epithelial immaturity; equivocal irregularity of epithelial surface |
| Moderate (2) | At least two foci of crypt branching or loss of crypts (<50%); loss of surface epithelium |
| Severe (3) | Diffuse or multifocal branching or loss of crypts (>50%); fibrosis; complete loss of epithelium (focal) |

Additional histologic assessment was performed using immunohistochemistry for the detection and semiquantification of lymphocytes expressing β7 integrins and mucosal venules expressing MAdCAM. As previously described (Ringler, D. J., et al., *Am. J. Pathol.* 134:373–383, 1989), colon tissue was first snap-frozen in OCT compound, sectioned while frozen, and the sections were subsequently fixed in acetone for 10 min at 4° C. After washing in phosphate buffered saline (PBS), nonspecific antibody binding sites were blocked with 10% normal rabbit serum diluted in PBS for 10 min, followed in sequence with washes by FIB21 antibody at 20 μg/ml in PBS for 30 min at room temperature (RT), biotinylated rabbit anti-rat polyclonal antibody, avidin-peroxidase complexes, and finally the chromogen, diaminobenzidine and hydrogen peroxide diluted in Tris buffer.

In the second method, recruitment of lymphocytes to the colon was quantitatively assessed using radiolabeled mesenteric lymph node lymphocytes from syngeneic donor mice. The experimental design of the animal experiments was similar to that described above except that BALB/c mice were placed on 5% DSS for 9 days (instead of 10) and on day 8, mice were given i.p. injections of 100 μg of FIB21 (anti-β7), MECA-367 (anti-MAdCAM), a mixture of both, or an isotype-matched control monoclonal antibody in saline. On day 9, mesenteric lymph node cells were isolated from donor syngeneic BALB/c mice, labeled with $^{51}$Cr, and $5.0 \times 10^6$ cells/mouse were incubated for 30 minutes at 37° C. with 500 μg control antibody, 250 μg of MECA-367, 500 μg FIB21, or both (total amount is 750 μg) in saline. The labeled cells and antibody were then injected intravenously (i.v.) into the DSS-treated recipient mice. Full-length colons were harvested from all experimental animals 1 hour after injection, and γ-irradiation was measured using a γ-counter.

Data Analysis

Differences between mean scores obtained for each group of animals were assessed for statistical significance using a paired Student's t-test. Differences between means were considered significant when $P<0.05$.

Results

Histologically, inflammation and epithelial injury to the mucosa were most severe in the descending colon, rectum and cecum. Analysis of frozen tissue sections of colon by immunohistochemistry revealed that the most significant recruitment of β7+ lymphocytes was to the right colon. In addition, the level of expression of the mucosal vascular addressin, MAdCAM-1, was found to be expressed only at low levels in vessels in the intestinal mucosa early in DSS treatment (3 days), but increased dramatically after 9 days of DSS treatment, supporting the conclusion that β7 and MAdCAM-1 interactions are relevant to the inflammatory process in the colonic mucosa during DSS-induced colitis.

Figure 1B:
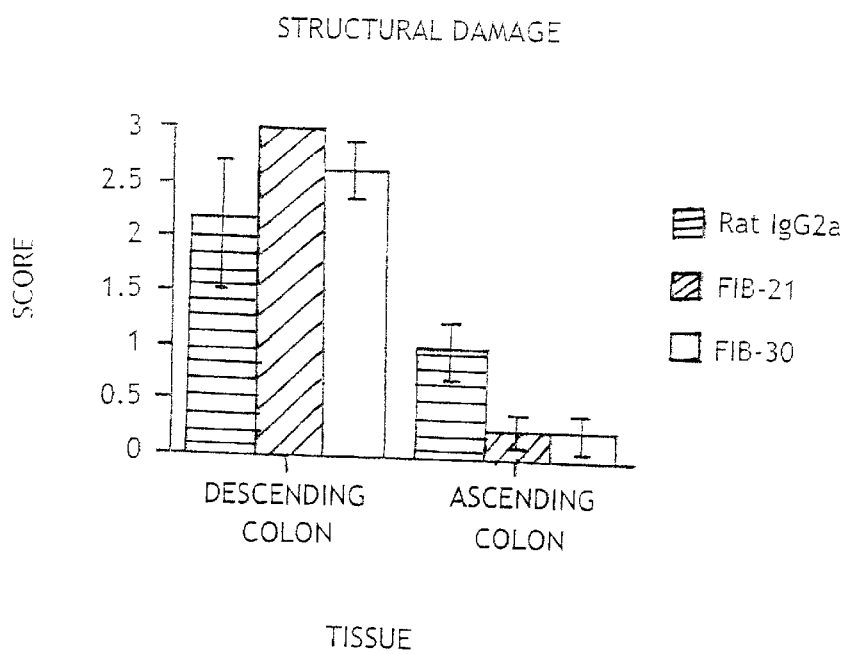

Histologic evaluation of mice exposed to a 10-day course of DSS and daily therapy using β7-specific antibodies demonstrated that substantial reductions of leukocyte recruitment ($P<0.0$ for FIB30 and $P<0.001$ for FIB21) and epithelial injury ($P<0.05$) occurred in right (ascending) colon compared to animals receiving a control antibody at the same dose (FIGS. 1*a* and 1*b*). Furthermore, analysis using immunohistochemistry of frozen sections from these animals suggested that the number of β7+ cells recruited to the right colon, but not other sections of colon, during DSS treatment was reduced.

Figure 2:
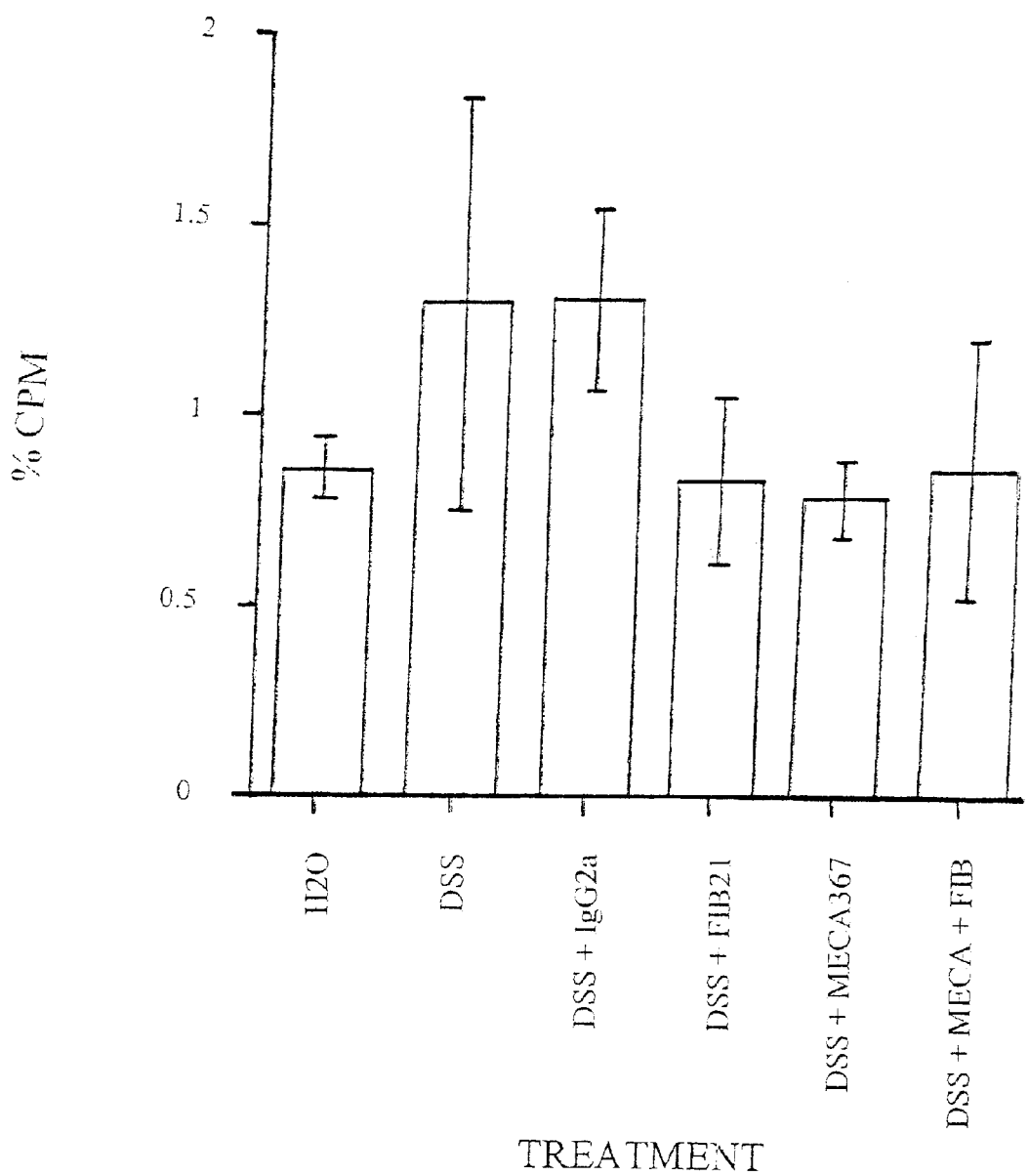
FIG. 2 is a graph of γ counts per minute (cpm) (±1 SEM) as a percentage of input from mice given DSS in the drinking water for 10 days. Six groups consisted of negative controls given water alone, positive controls given DSS alone, test groups given irrelevant rat IgG2a antibody, FIB21, MECA-367, and FIB21 with MECA-367.

Lymphocyte recruitment to inflamed colon was then quantitatively assessed using radiolabeled mesenteric lymphocytes taken from syngeneic donors. One hour after injection of these cells in DSS-treated recipients, there was a trend towards a reduction in the number of $^{51}$Cr-labeled cells recruited to colon in mice that were treated with either β7-specific antibodies or the MAdCAM-specific antibodies, but not in mice treated with the isotope-matched control antibodies (FIG. 2).

Example 2
Resolution of Villus Alterations in the Common Marmoset (*Callithrix jacchus*) with Malabsorptive Enteritis Description of Model Common marmosets (*Callithrix jacchus*) are a new world nonhuman primate that, under captive conditions at the New England Regional Primate Research Center (NERPRC), develop a steroid-nonresponsive, spontaneous malabsorption syndrome characterized by weight loss, diarrhea, and small intestinal mucosal changes consistent with loss of absorptive capacity. These histologic changes include small intestinal villus atrophy and fusion, and a mononuclear leukocyte infiltrate within the lamina propria similar to Celiac disease (nontropical sprue) in humans. Retrospective analysis from the pathology archive files at NERPRC demonstrated that up to 80% of common marmosets have, to various degrees, malabsorptive enteritis at the time of post-mortem examination.

Antibody Therapy Protocol

Adult common marmosets were selected for study from the colony-at-large at NERPRC. Base-line studies on all animals included physical examination, complete blood count (CBC), blood chemistry profile, serum B12, c-reactive protein, and full-thickness jejunal biopsy by laparotomy. Following recovery from abdominal surgery, the animals were treated for 14 days with 2 mg/kg/day of ACT-1 monoclonal antibody, a blocking monoclonal antibody against a conformational epitope of $\alpha 4\beta 7$ (Schweighoffer, T., et al., *J. Immunol.* 151:717–729, 1993). Previous studies indicated that this antibody cross-reacted to Callithrix $\alpha 4\beta 7$. All assessments that were performed prior to antibody therapy were repeated between the 10th and 14th day of antibody therapy.

Analysis of Jelunal Biopsies

Full-thickness jejunal biopsies from each marmoset were evaluated histologically by two independent pathologists, and villus architecture was scored according to the following grading criteria:

Villus atrophy
0—normal mucosal thickness and villus height
1—mild atrophy; slight shortening of villi; height approximately 75% of normal
2—moderate atrophy; villi approximately 33–50% normal height
3—severe atrophy; short (<33% normal) or no observable villi Villus fusion
0—normal; no fusion
1—1–2 villi in specimen fused
2—Between 1–2 and 50% of villi in specimen fused
3—>50% villi in specimen fused Data Analysis Differences between mean scores obtained for each group of animals were assessed for statistical significance using a paired Student's t-test. Differences between means were considered significant when P<0.05.

Results

Figure 3:
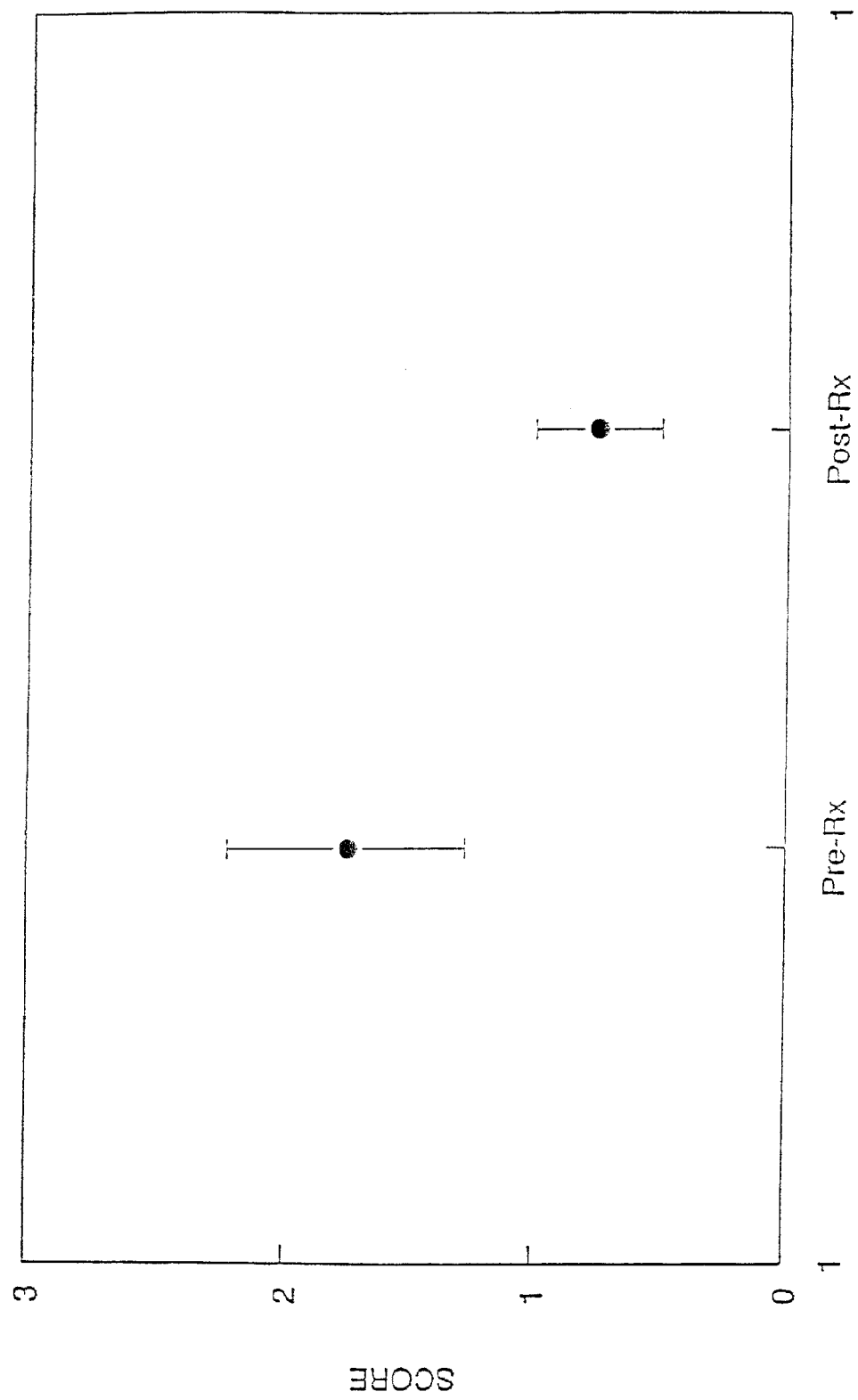
FIG. 3 is a graph depicting the histologic scores (±1 SEM) for villus fusion obtained from jejunal biopsy samples of common marmosets before and on the 14th day of treatment with 2 mg/kg/day of ACT-1 monoclonal antibody.
Figure 4:
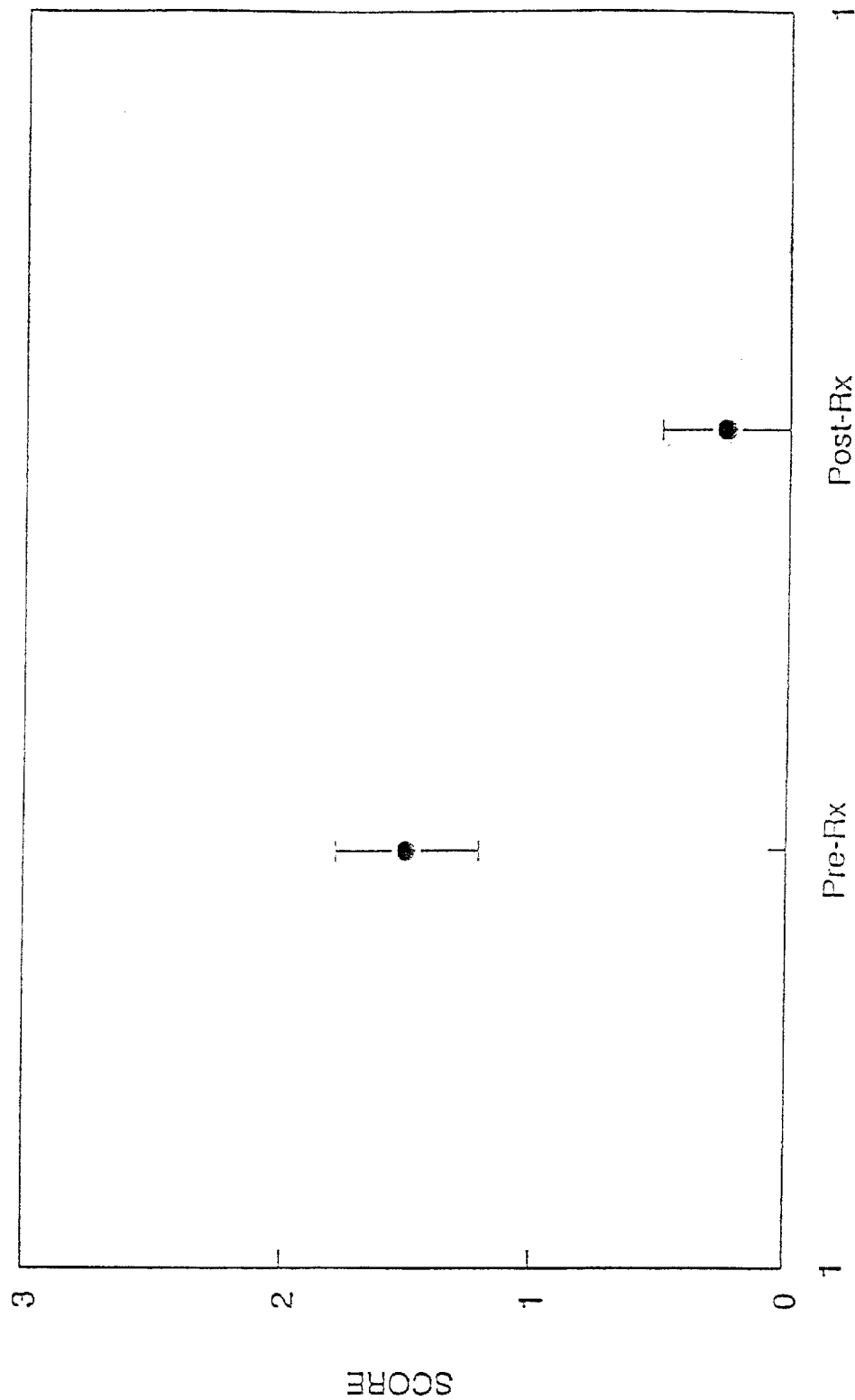
FIG. 4 is a graph depicting the histologic scores (±1 SEM) for villus atrophy obtained from jejunal biopsy samples of common marmosets before and on the 14th day of treatment with 2 mg/kg/day of ACT-1 monoclonal antibody.
Figure 5:
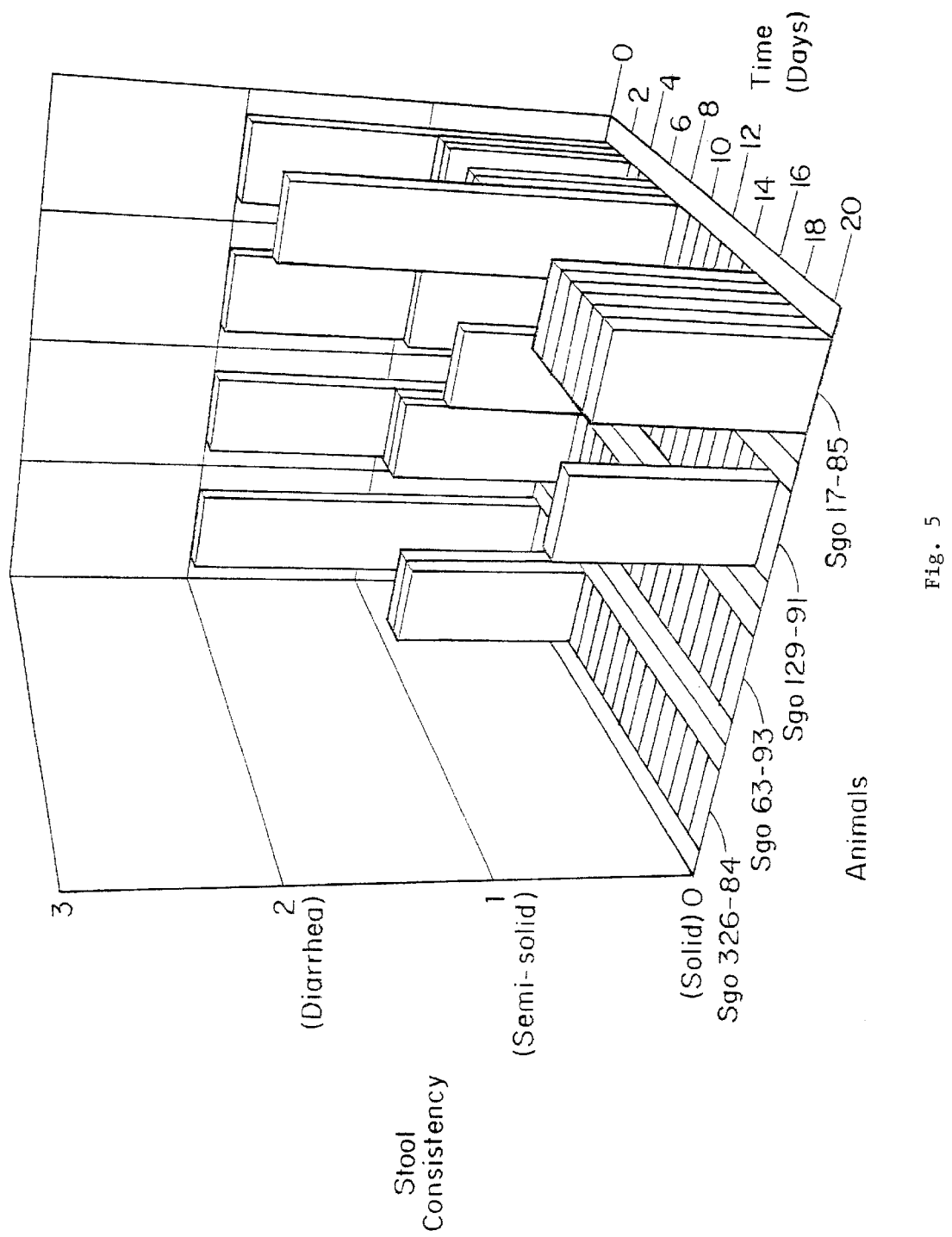
FIGS. 5 and 6 are graphic illustrations of the stool consistency and inflammatory activity in colitic animals (cotton-top tamarins) treated with ACT-1 antibody.

The mean scores for villus fusion and atrophy before and after antibody therapy with the ACT-1 monoclonal antibody are shown in FIGS. 3 and 4, respectively. As demonstrated, there was almost complete resolution of villus atrophy (P<0.01) and a trend for improvement of villus fusion after a two-week course of therapy with the ACT-1 antibody. The effect was not secondary to nonspecific effects of exposure to foreign immunoglobulin since other animals treated with various monoclonal antibodies directed against epitopes other than that recognized by ACT-1 were ineffective in reducing villus fusion and atrophy scores.

Example 3
Resolution of Colitis in the Cotton Top Tamarin

Description of Model

The cotton-top tamarin (*Saguinus oedipus*) is a New World nonhuman primate which develops a spontaneous colitis similar to ulcerative colitis in man.

ACT-1 was known to cross-react in the tamarin because of immunohistologic staining with ACT-1 antibody of colitic mucosa from affected animals. These initial pilot studies demonstrated that from 40–80% of mononuclear cells within the lamina propria of colon from affected animals were $\alpha 4\beta 7+$, similar to human colitic mucosa.

Methods

Colitic animals were chosen from the colony-at-large based upon gross observation of diarrhea and weight loss. All candidate animals were then subjected to colon biopsy to confirm the presence of colitis, as defined as a histologic inflammatory activity score of 2 or 3. The scoring system used was originally described in Madara, J. L. et al., *Gastroenterology* 88:13–19 (1985). Briefly, inflammatory activity scores were based upon the relative numbers of neutrophils within the lamina propria, crypt lumena, crypt epithelium, and surface epithelium. All biopsy samples were scored and categorized into four groups, with 0 representing normal mucosa and 3 representing the most severe and inflamed mucosa. Scores of 0 and 1 do not represent symptomatic colitis, while scores of 2 to 3 represent mild to severe colitic activity. Within 5 days of confirmation of colitis, the animals began immunotherapy with ACT-1 monoclonal antibody.

Four colitic animals received ACT-1 monoclonal antibody at a dose of 2 mg/kg/day intravenously (I.V.) the first day followed by intramuscularly (I.M.) injections for 7 consecutive days thereafter. The dosing regime was the same as that used in the common marmoset study above.

Colon biopsies were again obtained at the time of the first antibody infusion (Day 0) and on days 5, 10 and 20. The biopsies were evaluated by an independent pathologist. Additional colon biopsies were frozen for immunohistology. Animal caretakers evaluated stool consistency on a daily basis by categorizing stool as diarrhea, semi-solid, or solid. Animals were weighed every other day, while blood was drawn at the same intervals for flow cytometry, hematology, and storage of serum or plasma for further analyses, such as antibody concentration, anti-mouse IgG titer, clinical chemistry, or acute phase proteins.

Results/Progress

All four animals maintained either a grade 2 or 3 colitic inflammatory activity in both the pre-treatment and Day 0 biopsy samples, which for 3 animals was separated by 5 days. In addition, changes within the mucosal architecture of all four animals demonstrated that these four animals had colitis of a long-lasting nature. Therefore, all animals appeared to have a chronic disease course.

With respect to stool consistency, diarrhea resolved in all four animals by day 8 of ACT-1 immunotherapy (FIG. 4). All animals maintained solid stools for approximately 1 week after termination of antibody injections (FIG. 4). One animal (Sgo 63-93) has had solid stool from Day 4 until the end of the protocol at Day 20 (FIG. 4). Two animals (Sgo 129-91 and Sgo 17-85) had slight relapses to semi-solid stools after Day 14 in the study (FIG. 4). The fourth animal (Sgo 326-84) showed a persistent improvement/resolution of diarrhea from Day 6 to Day 20.

Figure 6:
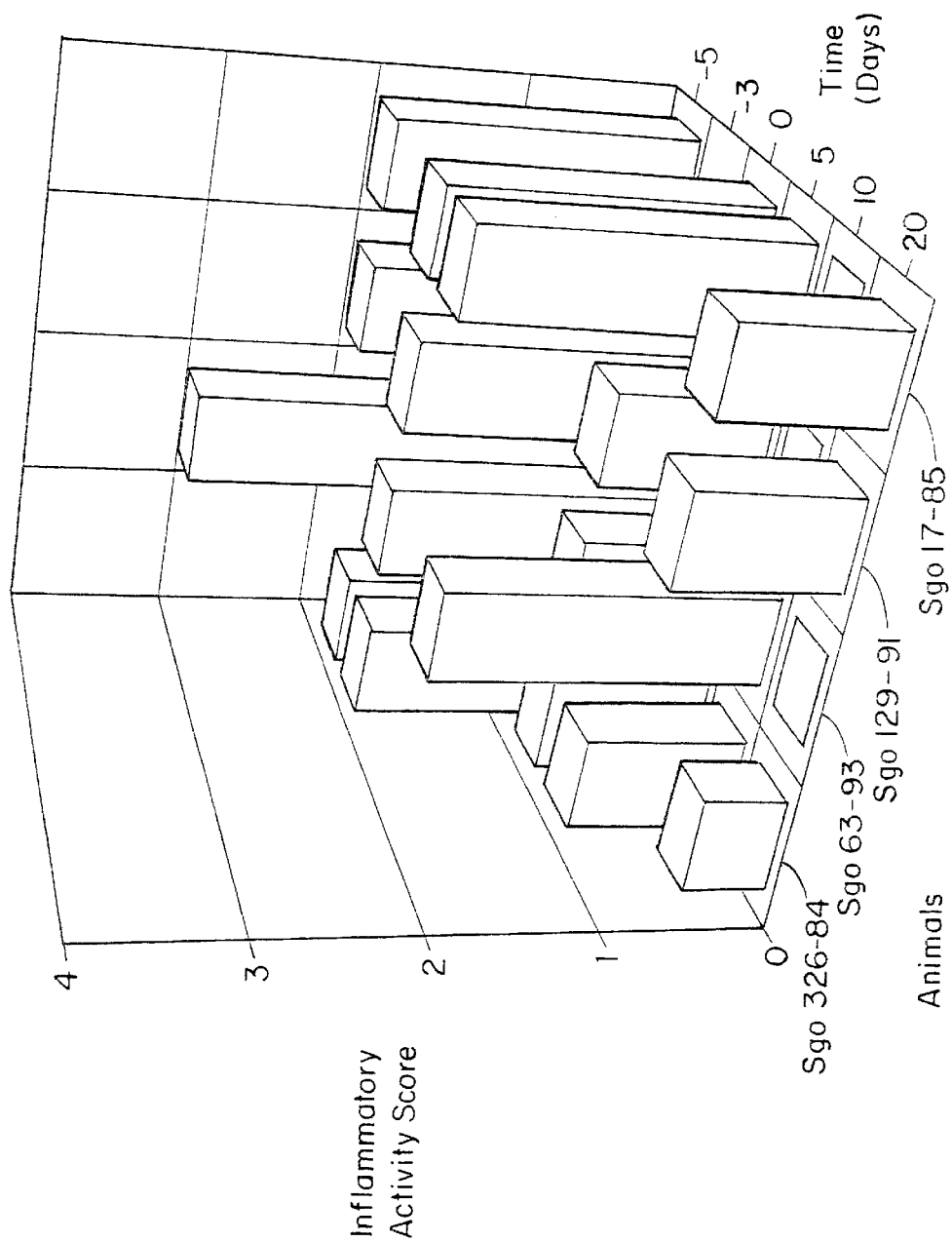

With respect to histologic changes, all four animals have shown improvement in inflammatory activity during or after ACT-1 immunotherapy. The colitis in two animals (Sgo 129-91 and Sgo 17-85) completely resolved by Day 10 (FIG. 6). Another animal (Sgo 63-93) did not show complete abrogation of colitis activity until Day 20 (FIG. 6), while mucosal biopsy scores from the fourth animal (Sgo 326-84) showed improvement during the entire study period (FIG. 6; two biopsies on day 20 in Sgo 326-84 were scored as 0 and 1). Furthermore, animal 326-84 gained 20% of its original body weight during the study period.

To detect antibody administered in vivo, flow cytometry and immunohistology were performed. Flow cytometry without a primary antibody showed excellent labeling to peripheral blood lymphocytes in animals at all time points after antibody administration. Immunohistology on colon biopsies using no primary antibody in the sequence from three animals on samples up to and including Day 10 showed excellent labeling of lymphocytes within the lamina propria on the samples from Days 5 and 10 but not, as expected, from Day 0 prior to antibody infusion. Collectively, these results showed that ACT-1 antibody localized to the target site, namely lymphocytes within the peripheral blood and specifically to the extravascular compartment within colitic mucosa.

Summary

By histologic criteria and stool consistency, ACT-1 was efficacious in improving colitis in the cotton top tamarin.

There appeared to be a good correlation between histologic inflammatory activity scores and stool consistency. Noteworthy is the observation that stool consistency generally improved in 1–2 days in animals receiving ACT-1 antibody.

EQUIVALENTS

Those skilled in the art will know, or be able to ascertain, using no more than routine experimentation, many equivalents to the specific embodiments of the invention described herein. These and all other equivalents are intended to be encompassed by the following claims.

What is claimed is:

1. A method for treating an individual having a disease associated with leukocyte recruitment to the gastrointestinal tract or other tissues as a result of binding of leukocytes to gut-associated endothelium expressing the molecule MAdCAM, comprising administering to the individual an effective amount of an antibody or antigen binding fragment thereof, said antibody or fragment having the epitopic specificity of the ACT-1 monoclonal antibody.

2. The method of claim 1 wherein a monoclonal antibody or antigen binding fragment thereof is administered.

3. The method of claim 2 wherein the monoclonal antibody or antigen binding fragment thereof is the ACT-1 monoclonal antibody or an antigen binding fragment thereof.

4. The method of claim 2 wherein the monoclonal antibody or antigen binding fragment thereof is selected from the group consisting of a chimeric antibody, an antigen binding fragment of a chimeric antibody, a humanized antibody and an antigen binding fragment of a humanized antibody.

5. The method of claim 1 wherein the leukocytes are lymphocytes.

6. The method of claim 1 wherein the leukocytes are monocytes.

7. The method of claim 1 wherein the disease is inflammatory bowel disease.

8. The method of claim 7 wherein the disease is ulcerative colitis.

9. The method of claim 7 wherein the disease is Crohn's disease.

10. The method of claim 7 wherein the disease is Celiac disease, enteropathy associated with seronegative arthropathies, microscopic or collagenous colitis, eosinophilic gastroenteritis, or pouchitis.

11. The method of claim 7 wherein the monoclonal antibody or antigen binding fragment thereof is the ACT-1 monoclonal antibody or an antigen binding fragment thereof.

12. The method of claim 7 wherein the monoclonal antibody or antigen binding fragment thereof is selected from the group consisting of a chimeric antibody, an antigen binding fragment of a chimeric antibody, a humanized antibody and an antigen binding fragment of a humanized antibody.

13. A method for treating inflammatory bowel disease in an individual comprising administering to the individual an effective amount of an antibody or antigen binding fragment thereof, said antibody or fragment having the epitopic specificity of the ACT-1 monoclonal antibody.

14. The method of claim 13 wherein a monoclonal antibody or an antigen binding fragment thereof is administered.

15. The method of claim 14 wherein the monoclonal antibody or antigen binding fragment thereof is selected from the group consisting of ACT-1 and an antigen binding fragment thereof.

16. The method of claim 14 wherein the monoclonal antibody or antigen binding fragment thereof is selected from the group consisting of a chimeric antibody, an antigen binding fragment of a chimeric antibody, a humanized antibody and an antigen binding fragment of a humanized antibody.

17. The method of claim 14 wherein the disease is ulcerative colitis.

18. The method of claim 14 wherein the disease is Crohn's disease.

19. The method of claim 14 wherein the disease is Celiac disease, enteropathy associated with seronegative arthropathies, microscopic or collagenous colitis, eosinophilic gastroenteritis, or pouchitis.

20. The method of claim 17 wherein the monoclonal antibody or antigen binding fragment thereof is selected from the group consisting of a chimeric antibody, an antigen binding fragment of a chimeric antibody, a humanized antibody and an antigen binding fragment of a humanized antibody.

21. The method of claim 18 wherein the monoclonal antibody or antigen binding fragment thereof is selected from the group consisting of a chimeric antibody, an antigen binding fragment of a chimeric antibody, a humanized antibody and an antigen binding fragment of a humanized antibody.

22. The method of claim 19 wherein the monoclonal antibody or antigen binding fragment thereof is selected from the group consisting of a chimeric antibody, an antigen binding fragment of a chimeric antibody, a humanized antibody and an antigen binding fragment of a humanized antibody.

* * * * *